(12) United States Patent
Siegal

(10) Patent No.: US 8,173,441 B2
(45) Date of Patent: May 8, 2012

(54) METHOD FOR APPLYING NMR FOR LIGAND DISCOVERY OR AS A DRUG SCREENING TOOL

(75) Inventor: Gregg David Siegal, Oegstgeest (NL)

(73) Assignee: Universiteit Leiden, Leiden (NL)

( * ) Notice: Subject to any disclaimer, the term of this patent is extended or adjusted under 35 U.S.C. 154(b) by 0 days.

(21) Appl. No.: 10/111,251

(22) PCT Filed: Sep. 27, 2001

(86) PCT No.: PCT/NL01/00711
§ 371 (c)(1),
(2), (4) Date: Aug. 26, 2002

(87) PCT Pub. No.: WO02/27309
PCT Pub. Date: Apr. 4, 2002

(65) Prior Publication Data
US 2003/0148297 A1    Aug. 7, 2003

(51) Int. Cl.
*G01N 24/00* (2006.01)
(52) U.S. Cl. .................................... 436/173; 505/844
(58) Field of Classification Search .............. 422/100, 422/103, 102; 436/173; 324/321, 303, 306, 324/307, 308, 309, 318, 200; 505/844
See application file for complete search history.

(56) References Cited

U.S. PATENT DOCUMENTS

| | | | | |
|---|---|---|---|---|
| 3,427,532 A | * | 2/1969 | Nelson | 324/308 |
| 4,646,024 A | * | 2/1987 | Schenck et al. | 324/318 |
| 4,654,592 A | * | 3/1987 | Zens | 324/307 |
| 5,162,739 A | * | 11/1992 | Doty | 324/322 |
| 5,283,036 A | * | 2/1994 | Hofmann et al. | 422/70 |
| 5,371,464 A | * | 12/1994 | Rapoport | 324/306 |
| 5,726,570 A | * | 3/1998 | Spraul et al. | 324/321 |
| 5,861,254 A | * | 1/1999 | Schneider et al. | 435/6 |
| 6,054,857 A | * | 4/2000 | Doty | 324/321 |
| 6,307,372 B1 | * | 10/2001 | Sugarman et al. | 324/321 |

(Continued)

FOREIGN PATENT DOCUMENTS
WO    94/03104    2/1994
(Continued)

OTHER PUBLICATIONS

TonThat et al., Low magnetic field dynamic nuclear polarization using a single-coil tow-channel probe, Rev. Sci. Instrum, vol. 68 (3), Mar. 1997.*

(Continued)

*Primary Examiner* — N. C. Yang
*Assistant Examiner* — Richard Moerschell
(74) *Attorney, Agent, or Firm* — Hoffmann & Baron, LLP

(57) ABSTRACT

The present invention relates to a method for screening compounds to identify compounds that bind to a specific target, comprising the steps of: (a) providing a target immobilized to a solid support; (b) generating a first NMR spectrum of the said compounds to be screened in the presence of the solid support without the target molecule immobilized thereto; (c) generating a second NMR spectrum of the said compounds to be screened in the presence of the solid support with the target molecule immobilized thereto; and (d) comparing said first and second NMR spectrum to determine differences between said first and second NMR spectrum. Further the invention relates to an NMR apparatus having arranged therein a particular NMR probe.

11 Claims, 3 Drawing Sheets

U.S. PATENT DOCUMENTS

| | | | |
|---|---|---|---|
| 6,677,160 B1 * | 1/2004 | Stockman et al. | 436/173 |
| 6,696,838 B2 * | 2/2004 | Raftery et al. | 324/321 |

FOREIGN PATENT DOCUMENTS

| | | |
|---|---|---|
| WO | 97/18469 | 5/1997 |
| WO | 97/18471 | 5/1997 |
| WO | 98/48264 | 10/1998 |
| WO | WO 98/57155 | 12/1998 |

OTHER PUBLICATIONS

Fisher et al., NMR Probe for the Simultaneous Acquisition of Multiple Samples, Journal of Magnetic Resonance, vol. 138, (1999) pp. 160-163.*

Stoll et al., Simple single-coil double resonance NMR probe for solid state studies, Rev. Sci. Instrum., vol. 48, No. 7, pp. 800-803, Jul. 1977.*

Klein (1999) J. Am. Chem. Soc. 121: 5336-5337.*

Klein (1999) J. Am. Chem. Soc., 121:5336-5337).*

Klein, et al., "Detecting Binding Affinity to Immobilized Receptor Proteins in Compound Libraries by HR-MAS STD NMR", *J. Am. Chem. Soc.* 1999, 121:5336-5337.

Hajduk, et al., "NMR-Based Screening in Drug Discovery," Quarerly Reviews of Biophysics, pp. 211-240, 32:3 (1999).

Hajduk, et al., "Discovering High-Affinity Ligands for Proteins," Science, pp. 497-499, 278:5337 (Oct. 17, 1997).

* cited by examiner

SEQUENCE LISTING

<160> NUMBER OF SEQ ID NOS: 1

<210> SEQ ID NO 1
<211> LENGTH: 26
<212> TYPE: DNA

-continued

```
<213> ORGANISM: Artificial Sequence
<220> FEATURE:
<223> OTHER INFORMATION: completely synthesized

<400> SEQUENCE: 1
atggcgaatc cgtaatcgga ttcgcc                                            26
```

METHOD FOR APPLYING NMR FOR LIGAND DISCOVERY OR AS A DRUG SCREENING TOOL

INCORPORATION OF SEQUENCE LISTING

Incorporated herein by reference in its entirety is the Sequence Listing for the above-identified Application. The Sequence Listing is disclosed in a computer-readable ASCII text file titled "Sequence_Listing.txt," created on Jul. 13, 2010. The sequence.txt file is 368 bytes in size.

FIELD OF THE INVENTION

The present invention relates to a method for applying nuclear magnetic resonance (NMR) for ligand discovery or as a screening tool, especially for drugs. More in particular, the invention relates to a method for applying NMR as a ligand discovery tool or as a screening tool to large or non-soluble target biomolecules. In more detail, the invention relates to a Target Immobilized NMR Screening (TINS) technique.

BACKGROUND OF THE INVENTION

The present invention intends to provide a method to detect interactions between molecules, and particularly small molecules, which typically have a molecular weight of 1,000 Dalton or less, and biomolecular targets. The targets typically or generally are biological molecules involved in a disease state and the aim is to find interacting molecules which may turn out to be potential drug candidates.

In day-to-day laboratory practice, current methods of drug discovery rely primarily on "serendipity screening" wherein large libraries of low molecular weight chemicals are systemically added to a target molecule and assayed in vitro for binding or inhibition of, e.g., enzymatic activity, or in vivo for a biological response. If binding is the sought-after-function, then typically such screening programs seek compounds that bind with high affinity, for instance in the nanomolar to micromolar range, and at the same time high specificity. In order to increase the chances of finding such compounds, the sizes of the libraries used for screening have expanded to encompass a million or more compounds nowadays. Screening such libraries is clearly time-consuming and requires very large quantities of the target molecule.

More in detail, presently, the primary method of de novo drug discovery is based on adding essentially a random collection of chemicals to a pharmacologic target and assaying for binding. This method has been termed serendipitous screening. Since the likelihood of finding an interaction between two molecules is roughly inversely proportional to the desired affinity, libraries of up to a million compounds or more are now typically used to maximize the chance of finding interactions with the sub micro-molar affinity required of a drug. Tremendous technological advances in "high-throughout screening" (HTS) have allowed the process to be streamlined to the level that some systems can screen up to 100,000 compounds per day.

These systems are generally based upon measuring the signal generated when a fluorescent or radioactively labelled chemical probe is displaced from the target. Although highly efficient, these systems have a number of limitations. Almost all depend upon the a priori availability of a ligand in order to begin target screening. As a result, so-called orphan receptors, that is targets for which no ligand is available, are generally beyond the scope of HTS systems. In addition, because of the need to displace a pre-bound ligand, HTS is generally only sensitive to high affinity interactions. The high affinity lead compounds derived from HTS screening are typically complex and exhibit multiple interactions with the target. As a result, performing structure activity relationship (SAR) analysis on the large quantity of data from an HTS screen can be the limiting step. Furthermore, optimisation of these leads for enhanced specificity/affinity/oral availability can also be difficult.

In WO-A-97/18471 and WO-A-97/18469, a new approach to identify ligands to target biomolecules using NMR is described. The method described is termed SAR-by-NMR ("structure activity relationship") and relies on the combination of serendipity screening and knowledge of the three dimensional structure of the target molecule. Instead of seeking both high affinity and high specificity ligands, the goal in these two applications is to find two non-mutually exclusive low affinity but high specificity ligands and chemically link these ligands together to form a high affinity ligand. NMR spectroscopy is used to detect the low affinity binding interactions, NMR being a technique ideally suited for that purpose. Changes in 2D-NMR spectra of the target molecule induced by ligand binding are detected.

More in detail, WO-A-97/18471 relates to a process for screening compounds to identify compounds that are ligands binding to a specific target molecule, said process is comprised of generating a 2D-$^{15}$N/$^{1}$H NMR correlation spectrum of a $^{15}$N-labelled target molecule; exposing the labelled target molecule to one or more chemical compounds; generating a second 2D-$^{15}$N/$^{1}$H NMR correlation spectrum; and comparing the two spectra to determine the differences.

WO-A-97/18469 discloses a process for designing a high affinity ligand, comprised of identifying at least two ligands to the target molecule, which bind to distinct binding sites on the target molecules, using multidimensional NMR spectroscopy; forming a ternary complex by exposing the at least two ligands to the target molecule; determining the 3D-structure of the complex formed and determining the spatial orientation of the at least two ligands; and using the spatial orientation determined to design the high affinity ligand.

The approach described in WO-A-97/18471 and WO-A-97/18469 was to use NMR to detect weak, but specific, interactions between the target, and more specific between a small, isotopically labelled protein, and the components of the compound library. The sensitivity of NMR to interactions of up to 1,000 fold lower affinity than required in the HTS methods means that in principle, 1,000 fold fewer compounds need be screened in order to equalize the chances of finding "hits". In practise, the library for an NMR screen is typically 100 times smaller. In addition to its smaller size, a library used for the "SAR-by-NMR" approach consists of much simpler compounds than the libraries used for HTS, with molecular weights generally below 300 Da. In this light, reference is made to the two following scientific articles of the group of the inventors mentioned in both international applications: Hajduk et al. in Quarterly Reviews in Biophysics 32 (1999) 211-240; and Hajduk et al. in Science 278 (1997), 12257-12261. The high specificity, low affinity lead compounds that result from such a screen can then be optimised by a variety of methods in order to produce realistic drug candidates.

SAR-by-NMR is a drug or ligand discovery system that can be carried out in its entirety by NMR. As such, it has a number of limitations. First, the target molecule must be available in large quantities (hundreds of mg to g) and must be isotopically labelled with either $^{15}$N or $^{13}$C, an impossibility with many targets. Second, the target should be less than roughly 30 kDa and be highly soluble and stable. Third, the resonance assignments for at least the backbone nuclei must be known and preferentially a 3D structure should be available. Furthermore, the target must be highly soluble and stable over a period of at least a few days to record the 2D-NMR spectra.

As an alternative approach to SAR-by-NMR, it is proposed to monitor the signals of the ligand instead of the target. Such an approach alleviates the constraints on molecular size and the necessity for isotopic labelling, but introduces other problems such as sensitivity and the need to re-optimize the system for every target. Additionally, large quantities of highly soluble target are still a prerequisite.

Such a method using NMR to identify ligands to target biomolecules is described in WO-A-98/57155. In this document, a method for identifying a drug core suitable for a given target is described, which method comprises providing a drug core consisting of a particular cyclic structure selected from a limited group. Thereto, the inventors of the invention described in this document propose to use one-dimensional solution NMR spectra to detect target-small compound interaction via changes in the spectrum of the small compound. The changes are detected via line broadening (a $T_2$ relaxation phenomenon) diffusion filters or 2D transferred NOE (Nuclear Overhauser Enhancement) spectra.

Another such alternative method using NMR to identify ligands to target biomolecules is described in WO-A-98/48264. It uses simple and well-known $^1$H-NMR spectroscopy to detect low affinity binding events by observing changes in the NMR spectrum of the potential ligand. This method, like the method describe in WO-A-98/57155, does not provide the 3D structural information that the SAR-by-NMR method does, but it does avoid the limits of a requirement for isotopically labelled target. More in detail, this known method requires the steps of generating a first $T_2$-relaxation filtered or diffusion-filtered proton-NMR spectrum of one or a mixture of chemical compounds; exposing the said one or more chemical compounds to the target molecule; generating a second $T_2$-filtered or diffusion-filtered proton-NMR spectrum of the exposed one or more chemical compounds; and comparing the differences in the spectra recorded to identify the presence of one or more compounds which have bound to the target molecule.

The latter two prior art methods cannot overcome the need for large quantities of soluble target material. In particular, these methods exclude membrane bound proteins, which form a large and attractive class of pharmaceutically interesting target molecules.

Moreover, the method of WO-A-98/48264 can only be used when the target is sufficiently larger than the small compounds to be assayed. Although the inventors in said WO-A state that the target can be as small as 5 kDa, the present inventor has carried out experiments which indicate that the limit of sensitivity is closer to 10 kDa. In addition, it is noted that the sensitivity of the method described in WO-A-98/48264 varies with each target to be screened.

In general, it is noted that NMR has significant advantages as a detection method for serendipitous drug screening including high sensitivity to weak interactions and no requirement for a priori knowledge of a ligand. However, present NMR methods have several limitations. The most severe of these limitations is the requirement for large quantities of soluble and stable pharmacological targets.

It is a primary aim of the present invention to provide a method having the advantages of the known NMR screening techniques, but not having all or part of the disadvantages associated with the above-discussed techniques.

SUMMARY OF THE INVENTION

This aim is reached by the method of the present invention which is based on the use of NMR to detect changes in the spectrum of potential binding compounds such as ligands. In this method, the target is immobilized on a solid support. This allows the entire screening process to be carried out in a flow-through manner on a single sample of target. All restrictions on the physico-chemical properties with respect to the target (e.g., size, solubility, stability or chemical composition) are alleviated. The target immobilized NMR screening method of the present invention demonstrates versatility and robustness with respect to a variety of targets which makes the system very useful for (commercial) drug discovery and the discovery of other compounds which interact with targets and especially target molecules.

More in detail, the present invention relates, in a first aspect, to a method for screening compounds to identify compounds that bind to a specific target, comprising the steps of:

(a) providing a target immobilized to a solid support;

(b) generating a first NMR spectrum of the said compounds to be screened in the presence of the solid support without the target immobilized thereto;

(c) generating a second NMR spectrum of the said compounds to be screened in the presence of the solid support with the target molecule immobilized thereto; and (d) comparing said first and second NMR spectrum to determine differences between said first and second NMR spectrum.

In a further aspect, the present invention relates to an NMR apparatus having arranged therein an NMR probe suitable for flow-through NMR screening of a test sample, said probe including a flow inlet, a first vessel which is connected to the flow inlet, a second vessel which is connected to the first vessel and a flow outlet which is connected to the second vessel, wherein one of the vessels includes a kind of carrier material including a kind of target molecule and the other vessel includes the said kind carrier material without the said kind of target material, wherein the NMR apparatus is arranged so as to include first means for generating a pulsed-radio field which at least extends into the vessels of the NMR probe, and wherein the NMR apparatus is arranged so as to include second means for measuring a first response in the said one vessel to the generated pulsed-radio field and a second response in the said other vessel to the generated pulsed-radio field.

DETAILED DESCRIPTION OF THE INVENTION INCLUDING THE BEST MODE

Figure 1:
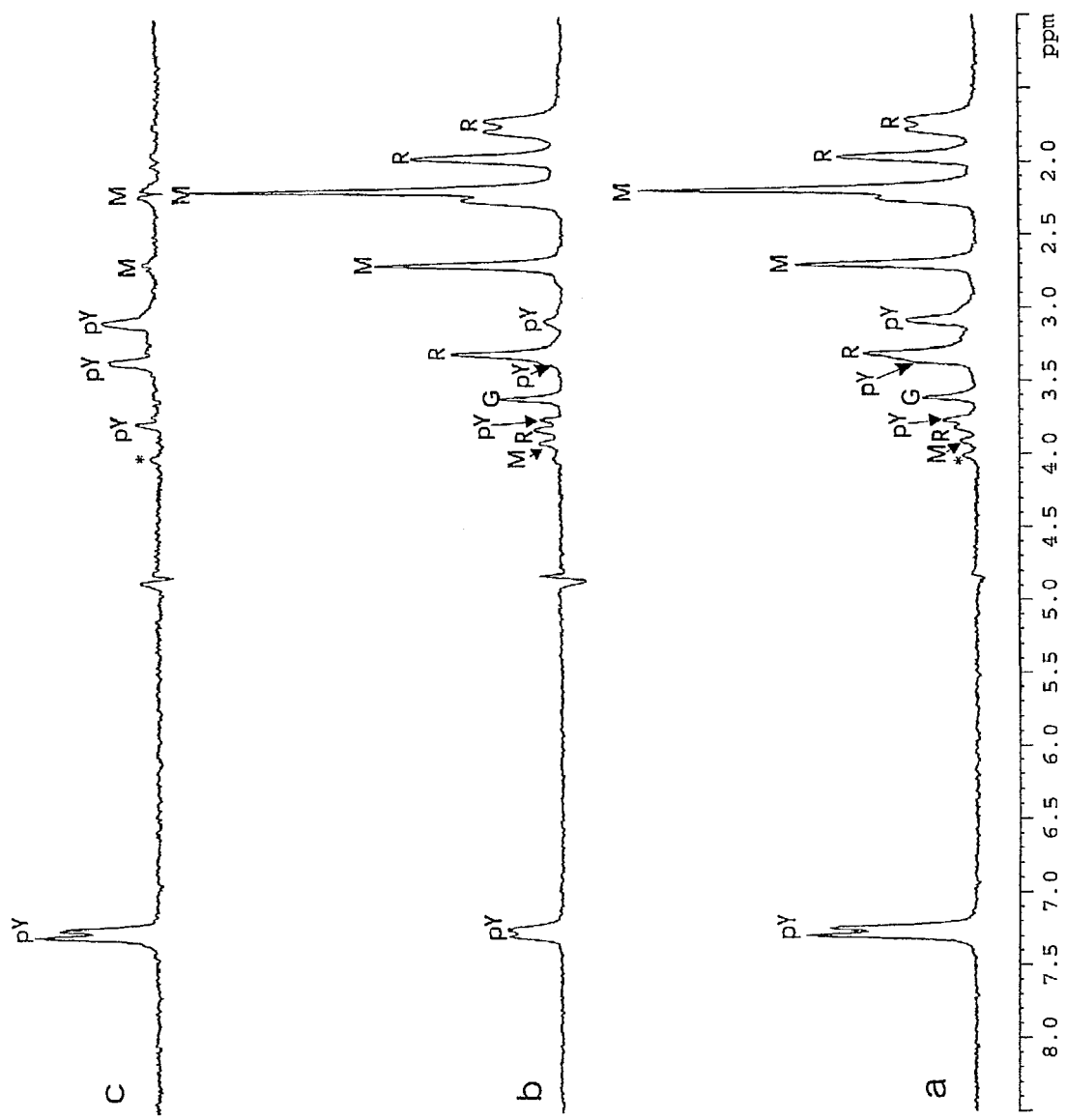
FIG. 1 shows $^1$H-NMR spectra of a mixture of phosphotyrosine, glycine, methionine and arginine dissolved in $D_2O$ (a) in the presence of a control derivatized resin and (b) in the presence of 500 µl of resin derivatized with 5.5 mg of CSH2. The same solution was used for each sample and NMR spectra were recorded with identical parameters. The difference spectrum is shown in FIG. 1(c); only peaks derived from phosphotyrosine, which is known to bind to CSH2, are seen in the difference spectrum.

As said herein-above, the present invention provides a method to detect binding of compounds to a target, and particularly to target (bio)molecules. Said method for screening compounds to identify compounds that are ligands, e.g., that bind to a specific target molecule, comprises the steps of: (a) a target molecule on a solid support; (b) measuring a reference NMR spectrum of one or more compounds suspected to be able to bind to the target molecule in the presence of a reference solid support, which does not contain the target molecule, yet may be derivatized with a non-target molecule or with a reference biomolecule, the reference NMR spectrum; (c) measuring an NMR spectrum of the same one or more compounds suspected to be able to bind to the target molecule in the presence of the solid support with the immobilized target molecule, the experimental NMR spectrum; and (d) comparing said experimental and reference NMR spectrum to determine differences between these two spectra.

A key aspect of the present invention is the binding of the target molecule to a solid support. This aspect can alleviate the limitations of the known NMR screening techniques. Particularly, in this configuration, rapid and sensitive NMR spectroscopy, and preferably one dimensional NMR spectroscopy and most preferably, $^1$H-NMR spectroscopy, can be used to monitor changes in the spectra of the compounds being screened due to target binding. This method in accordance with the present invention will be referred to in this description as TINS: for target immobilized NMR screening. As will be elaborated herein-below, the method of the present invention has been tested using a small protein and DNA as targets in order to demonstrate its versatility. TINS can detect specific binding characterized by a dissociation constant as low as about 10 mM using a single sample of the target. The method is easily quantified and thereby can afford approximate determination of binding constants. That is, the quantitation of the small compounds is accurate, yet precise quantitation is difficult; "approximate" binding constants (±10%) are determined, which are more than good enough for screening purposes. The target immobilized to a solid support can be placed in a flow-injection NMR probe and the components of a compound library, or components eluting from a fractionation column or a chromatography column etc. can be rapidly applied in an automated manner thus enabling true high-throughput screening of a wide variety of targets including orphan receptors.

Preferably, the NMR spectra measured are one-dimensional NMR spectra.

Because of the sensitivity and the ease of processing, preferably proton-(or 1H-)NMR spectra are recorded. Such spectra are about 16 times as sensitive as $^{13}$C-NMR and about 100 times as sensitive as $^{15}$N-NMR. However, also $^{13}$C-, $^{15}$N- and other known elements NMR spectra, and combinations thereof, such as combined $^{15}$N/$^1$H spectra can suitably be used in the method of the present invention.

Binding of a compound to the target molecule is detected by comparison of the NMR spectra with and without the target molecule for a diminution in the height of peaks deriving from the compound that binds.

Since these changes are most easily seen in the difference spectrum, step (d) of the method of the present invention is preferably and most suitably carried out by subtracting the first from the second spectrum or vice versa. Such a difference spectrum exclusively contains peaks derived form the compound that binds to the target.

In an alternative preferred embodiment, a quantitative analysis of binding can be obtained by comparison of the integrated peaks in the control and experimental spectra.

In order to detect very weak binding or compound-target molecule interactions, the skilled person has available and could employ a diffusion filter or a filter based on NMR relaxation ($T_2$ filter).

The target typically, but not necessarily, is a (bio)molecular target; for instance typically a biological molecule or a collection of molecules involved in a particular disease state is used. However, it is also possible to use all kinds of receptors, for instance, receptors involved in the sensory perceptions, which is suitable in order to find new aroma ingredients or flavor components. Suitable target molecules can, for instance, be DNA or RNA fragments, protein fragments, sugar moieties, oligo and poly amino acids, receptors, ribosomes, hormones, enzymes, etc., and combinations of these such as ribonucleoprotein particles, or other collections of molecules. The target immobilization results in the realization of a number of advantages: the range of possible target molecules is broadened to include virtually any molecule of interest, including for instance insoluble proteins, such as membrane proteins, which cannot be used as targets in the known NMR screening techniques. There is no restriction on the size of the target. A far smaller amount of target is required in relation to the amounts required in the known NMR screening techniques. For instance, for target proteins a single sample concentration of about 0.5 mM immobilized protein in the NMR probe already gives suitable results. Moreover, the stability of the target molecule is enhanced by the coupling to a solid support, while artefacts or other problems due to, e.g., protein aggregation are reduced and the speed of the screening process is enhanced.

Figure 2:
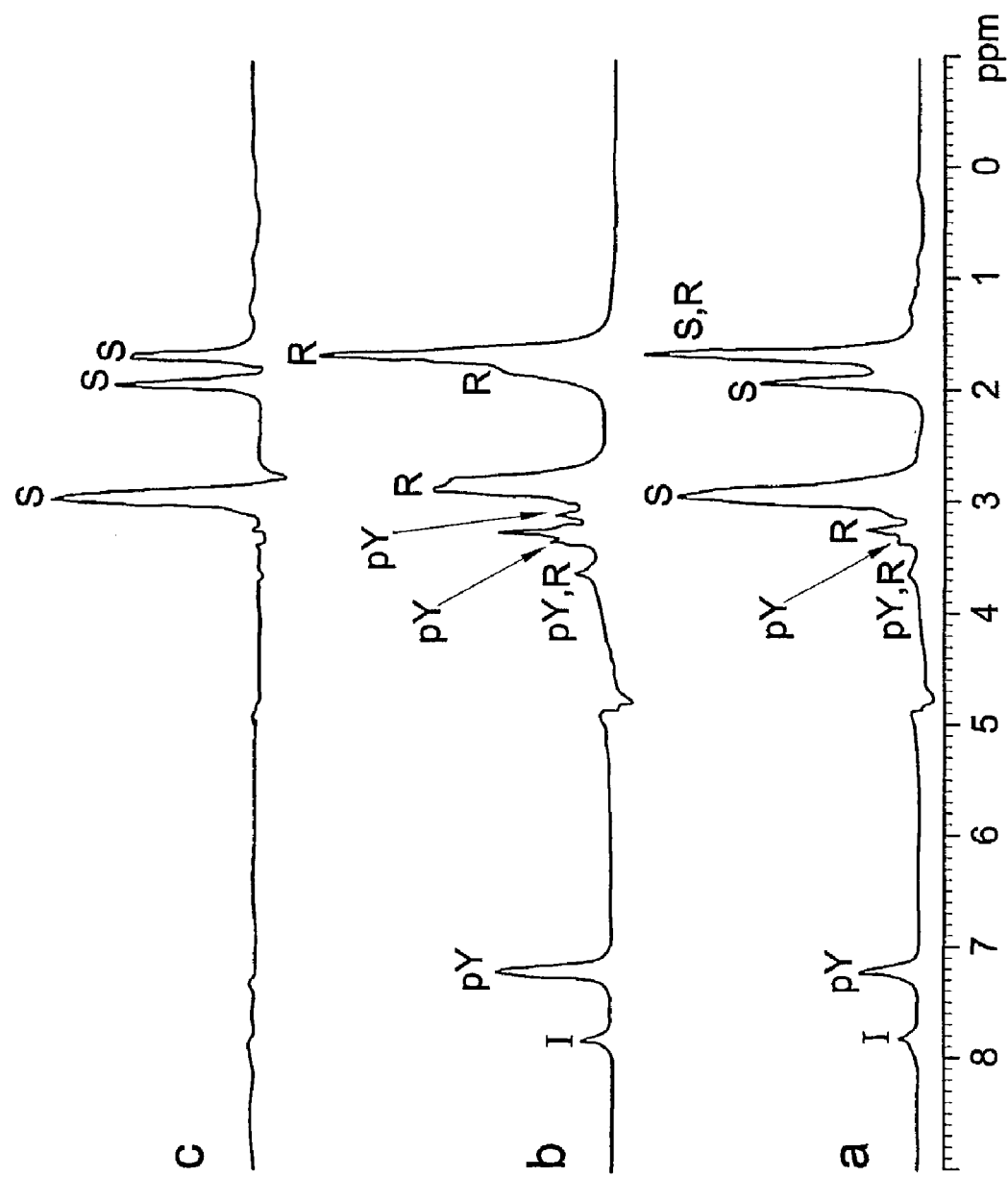
FIG. 2 shows $^1$H-NMR spectra of a mixture of spermine, phosphotyrosine, imidazole and arginine dissolved in $D_2O$ a) in the presence of a streptavidin sepharose resin and b) in the presence of 500 µl of streptavidin-sepharose resin with 4 mg of a synthetic oligonucleotide bound. The difference spectrum is shown in c. Only peaks derived from spermine, a known DNA binding molecule, are observed in the difference spectrum.

The target molecules can be immobilized to all types of solid supports. It is not needed that the binding is a covalent binding. Also non-covalent binding of, e.g., the high affinity binding type is suitable (cfr. FIG. 2). It is only required that the target is kept immobilized in the NMR measuring environment. Moreover, the immobilization need not be directly to the solid support; it may also occur indirectly through suitable bridging moieties or molecules, or through spacers. Very suitable supports are solid polymers used in chromatography, such as polystyrene, sepharose and agarose resins and gels, e.g. in bead form or in a porous matrix form. Additionally, appropriately chemically modified silicon based materials are also very suitable supports.

In fact, any soluble molecule can be used as a compound that is a candidate to binding to the target. It is not necessary that the said soluble molecule is water-soluble. Any liquid medium that does not denature the said compound nor the target molecule can be used in the NMR measurements. This makes the method of the present invention very flexible.

Preferably, the soluble molecules used as binding candidates are small molecules having a molecular weight of less than about 1,000 Da; however, the method of the invention is in principle not limited to a particular maximum size for the binding candidate compounds.

The use of an immobilized target molecule together with screenable dissolved compounds gives a system that is tolerant to variations in sample preparation, such as differences in pH and solvent. Thus, the system used in accordance with the present invention allows each test compound to be dissolved in a solvent that is optimised for its chemical nature, e.g. with respect to hydrophobicity, stability etc.

Furthermore, the methodology and sensitivity of the present method is highly consistent from one target molecule to another regardless of the nature of the target molecule, due to its immobilization on a solid support.

In the practice of the invention, the target molecule is immobilized to a suitable support, such as a solid resin, and additionally placed in a suitable NMR probe, and preferably a flow injection NMR probe, for the duration of the screening. Each sample of the compounds to be screened, e.g. the compounds from a library, is then applied to the immobilized target by pumping it through, along or via the solid support. The sample to be assayed may contain a single component suspected of binding to the target molecule, or may contain multiple components of a compound library or other type of collection or mixture. The flow may be stopped when a desired level of concentration of the compounds to be assayed is reached in the target containing probe or vessel.

For the acquisition of the NMR spectra, in principle any NMR pulse sequence capable of detecting resonances from dissolved molecule samples and, preferably suppressing residual solvent signals, such as by pulsed field gradients, may be used to detect binding. In practice, however, a one-dimensional $^1$H-NMR spectrum is acquired with sufficient resolution and sensitivity to detect and quantitate resonances derived from each compound being assayed in the presence of the control solid support. In addition, a second spectrum recorded using the same NMR protocol, is acquired for the same solution of screenable compounds in the presence of the solid support containing the immobilized target molecule.

Optionally, a third spectrum may be acquired in the presence of the solid support containing the immobilized target molecule in order to detect extremely weak target binding. This spectrum can be recorded while using a diffusion or $T_2$ filter.

After acquisition of the NMR spectrum, the sample of small compound or compounds is washed out of the NMR probe containing the target immobilized solid support. Subsequently, the next sample can be applied to the probe in a stopped-flow manner. Throughout the entire screening process a single sample of the target immobilized solid support remains in the NMR probe. The target immobilized solid support need only be changed should the target become denatured, chemically degraded or saturated by a tight-binding compound that cannot be washed away.

In order to safeguard that certain compounds do not bind in such a way that the target molecule is blocked, it is preferred that at certain stages, a control is carried out to check the availability of binding opportunities to the target molecule.

The NMR spectra are preferably compared by subtracting one of the two NMR data sets from the other, thereby creating a difference spectrum. In general, since the target molecule is essentially in the solid phase, the resonances from compounds that bind to the target molecule are broadened beyond detection while in the bound state. Thus, binding is sensitively and reliably detectable by a decrease in height of peaks that derive exclusively from the solution form of compounds binding to the target molecule. This effect is most easily seen in the difference spectra.

An alternative approach that can be used to quantitate the affinity of the target-ligand interaction is to determine peak areas (e.g. by integrating) in the control and experimental spectra and compare the values of these areas.

Although it is possible to carry out the screening method of the present invention in batch mode, one major advantage of the TINS methods of the present invention is that these methods allow screening to be performed in the flow-injection mode. All NMR screening methods known at the moment that the present invention was made, could only be carried out in the batch mode. In this flow-injection set-up, one sample of target may be used to screen an entire library.

Moreover, the speed of the process is greatly enhanced as the time consuming process of making up samples in individual tubes and placing them in the instrument for analysis in the batch mode is eliminated.

Additionally, the NMR experiments, and especially the one-dimensional experiments are faster and more sensitive than the more complex experiments utilized in the known NMR screening techniques.

The advantages mentioned in the previous paragraphs make the method of the present invention a true high-throughput screening method.

In a preferred embodiment, which forms a second aspect of the present invention, the method is carried out while using an arrangement that makes it possible that the sample to be screened is contacted with the solid support without and with the target molecule in series.

In a second embodiment of the invention, the first and second NMR spectra are acquired by using a probe comprising 2 chambers, wherein one of these chambers contains said solid support without the target molecule immobilized thereto, and the other chamber contains said support with the target molecule immobilized thereto, introducing the sample to be screened in the first chamber, recording the first NMR spectrum in said first chamber, introducing said sample to be screened in the second chamber and recording the second NMR spectrum in said second chamber.

In a preferred embodiment of this method, the sample is introduced in the first and second chamber in a stopped-flow mode.

Beside the advantages of the first embodiment, this second embodiment has the additional advantage that the reference and experimental spectra are recorded at about the same time using the same solution of screenable molecules thus eliminating artefacts due to instrumental, environmental and/or sample variations.

In a further aspect, the present invention also relates to an NMR apparatus having arranged therein an NMR probe suitable for flow-through NMR screening of a test sample, said probe including a flow inlet, a first vessel which is connected to the flow inlet, a second vessel which is connected to the first vessel and a flow outlet which is connected to the second vessel, wherein one of the vessels includes a kind of carrier material including a kind of target molecule and the other vessel includes the said kind carrier material without the said kind of target material, wherein the NMR apparatus is arranged so as to include first means for generating a pulsed-radio field which at least extends into the vessels of the NMR probe, and wherein the NMR apparatus is arranged so as to include second means for measuring a first response in the said one vessel to the generated pulsed-radio field and a second response in the said other vessel to the generated pulsed-radio field.

As said, in a preferred embodiment, a flow-injection NMR probe is used which comprises two small (contents less than 200 μl) chambers in-line that will hold the control and experimental solid supports, and especially the control and experimental resins, respectively.

Two separate coils, for example, are then able to independently and, preferably even simultaneously, record $^1$H spectra of the compounds to be tested for binding. This enables a highly efficient and automatable system wherein screenable samples can be injected via a sample preparation robot and sequentially be pumped through, via or along the solid supports in the NMR spectrometer. Having for instance 10 compounds per sample, this system can comfortably screen 100,000 compounds in one week using only a few milligrams of the target.

Figure 3:
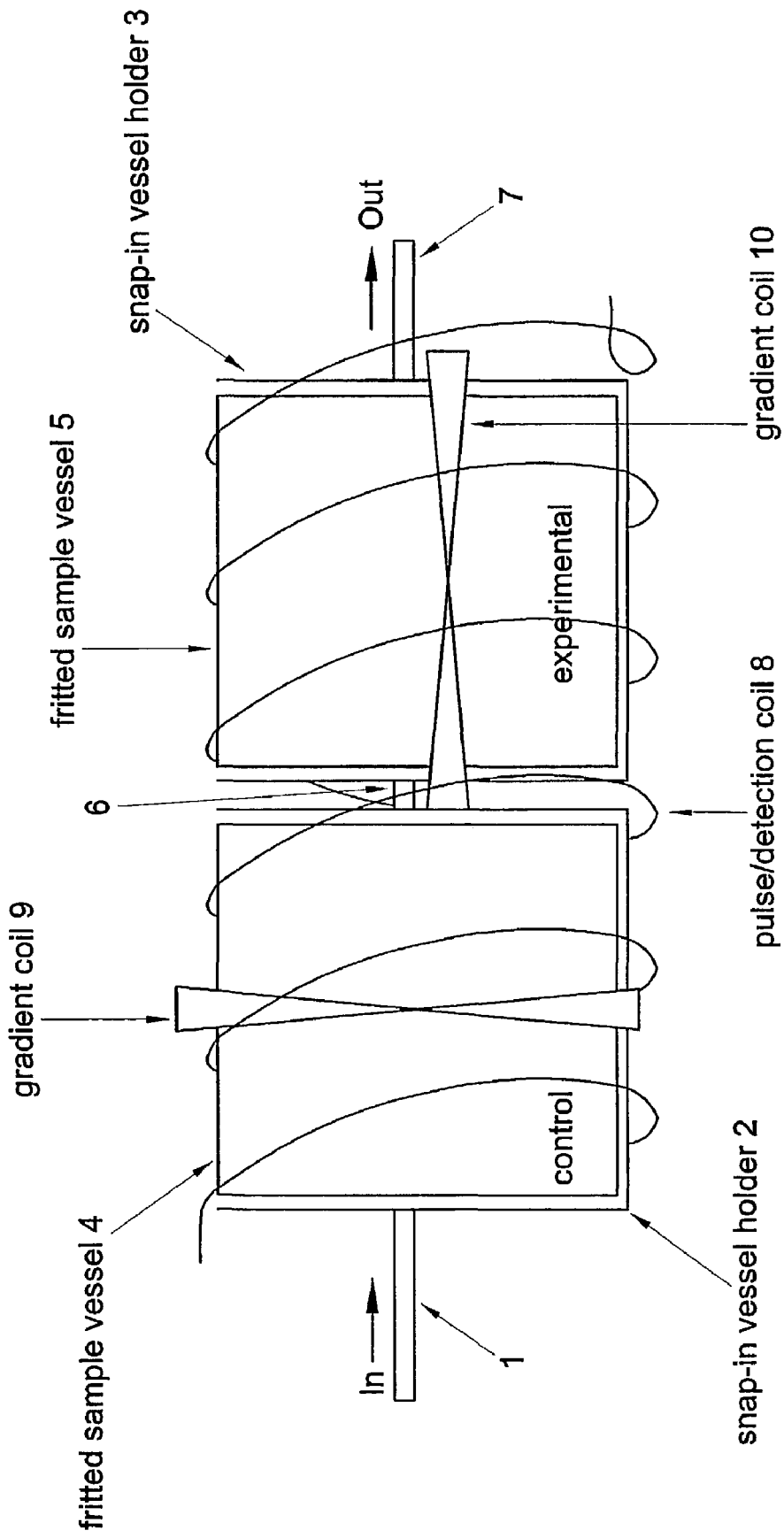
FIG. 3 shows a schematic drawing of a possible implementation of the NMR probe useful in the method of the present invention.

More in detail, the NMR apparatus is further described while referring to FIG. 3. FIG. 3 is a schematic drawing of one possible implementation of an NMR probe optimized for the flow-through method according to the present invention. The device consists of a flow inlet (1) connected to a pump (not shown) for applying the sample to be screened, two vessel holders (2 and 3) into each of which is placed a flitted sample vessel (4 and 5), tubing (6) connecting the two flitted vessels (4 and 5) and an outlet tube (7), where the sample can be sent to waist or for collection and recycling. The assembly must be placed in an NMR apparatus inside a pulse/detection coil (8) and two gradient coils (9 and 10). Sample vessel 4 may contain the control solid support without target molecule, while sample vessel 5 may contain the experimental solid support with target molecule and vice versa. The mixture of screenable compounds is pumped through both vessels. NMR spectra are separately recorded for the sample in sample vessel 4 and for the sample in sample vessel 5.

In one preferred embodiment, two independent pulsed-field gradient coils (9 and 10) are used for each vessel, and one detection coil (8) is used. The two independent pulsed-field gradient coils can be used to selectively destroy phase coherences in one sample vessel.

In another preferred embodiment, a separate pulse detection coil is used for each vessel.

As said, generally, difference NMR methods are sensitive to potential variations in experimental conditions such as changes in the concentration of ligand or target, temperature, pH etc. These changes can lead to artefacts in the difference spectrum thus complicating data analysis. However, the TINS system of the present invention described above greatly minimizes these potential problems due to the fact that the same solution of test compounds is applied to both the control and experimental resins. Furthermore, both spectra are acquired at about the same time on samples physically adjacent to each other, which minimizes any possible variation in temperature or drift in spectrometric conditions.

By focussing on small molecules, having molecular weights of less than about 1,000 Da, the system allows much greater flexibility in the choice of solvents and pH used to dissolve the test compounds while attachment alleviates the requirement for soluble target and in many cases will actually help to stabilize the target. Finally, the TINS method allows one to measure only specific binding by using known non-specific drug binders such as human serum albumin in the control chamber during the actual drug screening process. A solution mode of screening would not be capable of detecting such differences.

As said, the present invention realizes a number of advantages for ligand screening processes that could not be seen a priori. The method of the invention has a number of technological aspects that render it advantageous to screen large numbers of potential ligands. First is the simplicity of the data. Since a ligand, when bound to the target molecule is effectively in the solid state, its NMR signals found to be broadened beyond detection. Therefore, target bound ligands do not contribute to the observed NMR spectrum. In other words, the NMR spectrum contains signals only from molecules that are in solution. In a simple one-dimensional spectrum, if a compound binds to the immobilized target, the only effect on the spectrum is a reduction in the peak height of resonances deriving from said compound. In essence, this makes the method of the present invention reduced to binary simplicity. This, of course, makes interpretation of data, especially the enormous amounts of data generated in a high-throughput screening much simpler.

The second advantage is sensitivity. The method of the present invention can detect binding interactions as weak as about 10 mM. The conditions of the screening can be modified to change this limit of detection as desired. For example, it is possible to raise the amount of immobilized target molecules and/or to lower the concentration of the compounds in the solution to be screened, which results in a decrease in the minimal affinity of an interaction that can be detected, since a greater proportion of the soluble compound will be bound to the target. Since the chance of finding a binding ligand is inversely proportional to the affinity of the interaction, the method of the present invention is about 100-1000 fold more likely to find ligands than known screening methods which can detect interactions characterized by the dissociation constants in the low micromolar range.

The present invention is now described in more detail, while referring in the following non-limiting examples.

EXAMPLE 1

A solution of 1 mM each of phosphotyrosine (pY), arginine (R), methionine (M) and glycine (G) was prepared in $D_2O$, 20 mM deuterated Tris-buffer (pH 7.5) and 50 mM NaCl.

A 1D $^1H$ spectrum was recorded on a 600 MHz Bruker DMX spectrometer (Bruker, Germany) using a WATERGATE pulse sequence to suppress residual solvent resonances (see Piotto et al. J. Biomol. NMR 2 (1992), 661-665).

A second 1D $^1H$ spectrum was recorded using the same solution, but in the presence of 500 µl of Actigel ALD (Sterogenem Carlsbad, Calif., USA) chromatography resin. It was found that the linewidth of the $^1H$ resonance increases by nearly 50 fold (from 0.5 to 25 Hz) in the presence of the resin. Nonetheless, the spectra acquired in the presence of resin still exhibit sufficient resolution to clearly see every peak and can be obtained in less than a minute.

EXAMPLE 2

In this example, it was aimed to investigate whether binding of a small molecule to a target bound to the resin would be detectable in the $^1H$ spectrum. The test system utilized the C-terminal SH2 domain (CSH2) from the 85 kDa, alpha form of the regulatory subunit of bovine phosphoinositide 3' kinase. This small (110 residues) protein domain has well characterized binding specificity. High affinity binding (Kd~100 nM) is observed for a peptidic ligand consisting of phosphotyrosine (pY)—valine or methionine—x-methionine (where x can be any amino acid residue).

To see whether the method of the present invention provides a mode appropriate for efficient screening of a large library of compounds, CSH2 was immobilized on a chemically activated chromatography resin of Actigel ALD by covalent attachment. Attachment occurs via primary amines on the surface of CSH2 as described in the manufacturers literature and therefore is (approximately) randomly oriented.

In detail, the c-terminal SH2 domain of p85alpha was prepared as previously described by Siegal et al. in J. Mol. Biol. 276(1998), 461-478. 11 mg of this domain CSH2 in a buffer consisting of 25 mM HEPES pH 7.5 and 100 mM NaCl was incubated with 1 ml of Actigel ALD (Sterogene, Carlsbad, Calif., USA) according to the manufacturers protocol. This amount corresponds to a 1 mM solution concentration. Unbound sites on the gel were blocked using $d_{11}$-Tris (Cambridge Isotopes, Andover, Mass., USA). The control resin was derivatized exclusively with $d_{11}$-Tris.

The potential ligands were dissolved in 99% $D_2O$ with $d_{11}$-Tris. For testing binding to the CSH2 derivatized resin, the solution consisted of 1 mM each of phosphotyrosine (pY), methionine (M), glycine (G) and arginine (R) in 25 mM Tris, pH 7.5 and 50 mM NaCl.

In all cases, the control and experimental target containing resins were washed three times with the same mixture of test substances.

All NMR spectra were recorded on a Bruker (Bruker, Germany) DMX 600 spectrometer. Spectra typically consisted of 16 to 64 transients of 2 k complex points, were apodized using a $\sin^2$ function and automatically baseline corrected using the supplied XWINNMR software provided by the manufacturer, Bruker, and methods described in the manufacturers literature. Difference spectra were also calculated using XWINNMR From the point of view of solution state NMR spectroscopy, the bound protein is essentially in the solid state and therefore exhibits undetectably broad resonances so that the $^1H$ spectrum of the CSH2 derivatized resin is nearly the same as that of control resin derivatized with deuterated Tris (not shown). A mixture of pY, M, G and R dissolved in $D_2O$ was then applied to the control resin and the resin with CSH2 covalently bound. $^1H$ spectra of each were recorded using identical parameters (FIGS. 1a and b). Visual inspection of the spectra indicates a clear diminution of the peaks derived from pY (most clearly visible in the peaks from the aromatic protons between 7.2 and 7.3 ppm) in the spectrum recorded in the presence of the immobilized CSH2. Subtraction of the spectra in FIG. 1a and FIG. 1b enhances the differences (FIG. 1c). Here all five unique resonances of pY can clearly be observed. In addition, small residual peaks from the β, γ and δ protons of M can be observed. In contrast, all peaks derived from protons of glycine and arginine, which do not bind CSH2, are completely removed.

More in detail, FIG. 1 shows the 1D $^1H$ NMR spectra of a 1 mM solution of pY, R, M and G in $D_2O$, 20 mM $d_{11}$-Tris (pH 7.5) and 50 mM NaCl. FIG. 1a shows the spectrum recorded in the presence of control derivatized resin. The spectrum shown in FIG. 1b is recorded in the presence of 5 mg of the SH2 domain covalently attached to the solid support. The preferred ligand for the SH2 domain is a short peptide consisting of phosphotyrosine (pY)—valine or methionine—x-methionine (wherein x can be any amino acid residue). pY is a mimic of the natural ligand of the SH2 domain and binds with a Kd of approximately 0.6 mM. Its resonances are marked with pY. R and G do not bind. M mimics the methionine residues in the natural ligand, but would be expected to bind with very low affinity (Kd≧10 mM). Peaks deriving from methionine are marked by M.

FIG. 1c shows the difference spectrum of spectrum 1a minus spectrum 1b. This spectrum shows only resonances from compounds that specifically bind the protein target. Thus the pY peaks are large reflecting relatively tight binding. Weak binding of M by the SH2 domain can be detected in the form of small residual peaks in the difference spectrum marked with an M. The asterisk denotes a low level pY containing contaminant in the commercial preparation.

EXAMPLE 3

A particularly exciting aspect of the TINS methodology is that it is routinely applicable to a wide variety of targets. Since the method is only sensitive to the amount of small molecule bound by the target, the nature of the target has little or no effect on the procedures required for screening. It, in principle, suffices to know how much of the target has been immobilized and then simply adjust the concentration of the compounds applied in order to detect binding of a desired affinity, but make no other changes, in order to begin screening a new target. To prove this, the protein target of example 2 was replaced with DNA.

Thereto, a 26 base oligonucleotide was synthesized and biotin labelled at the 5" terminus. The oligonucleotide was bound to streptavidin-sepharose resin and a mixture of small compounds containing spermine was applied to it and a control sample containing only the resin. Spermine is known to bind with moderately high affinity to the phosphate backbone of DNA. FIG. 2 demonstrates that binding of spermine to the oligonucleotide can be detected using exactly the same procedure as with protein.

More in detail, desalted biotinylated oligonucleotide (4 mg, sequence ATGGCGAATCCGTAATCGGAT TCGCC) (SEQ ID NO: 1) was dissolved in a buffer of 20 mM sodium phosphate pH 7.5, and 150 mM NaCl and incubated with 1 ml of Streptavidin-Sepharose (Pharmacia, Uppsala, Sweden) for 30° at room temperature. The resin was then washed 5 times with 99% $D_2O$ to remove unbound material.

Thereafter, the samples were subjected to the same NMR method as used in example 2.

In FIG. 2, the 1D $^1H$ NMR spectrum of a 1 mM solution of pY, R, Imidazole (I) and spermine (S) in $D_2O$ is shown. FIG. 2a is the spectrum recorded in the presence of streptavidin-sepharose resin. The spectrum in FIG. 2b is recorded in the additional presence of the 26 base synthetic double stranded 5' biotinylated oligonucleotide bound to the streptavidin sepharose resin. Spermine is known to bind to the phosphate backbone of DNA. R, pY and I do not bind DNA. The arginine resonances are marked by R, the visible imidazole resonance is marked by I and the resonances for phosphotyrosine are marked by pY. From the difference spectrum shown in FIG. 2c, it can be seen that only spermine peaks remain.

The invention claimed is:

1. An NMR apparatus comprising an NMR probe suitable for flow-through NMR screening of a test sample,
    wherein said apparatus comprises a probe;
    wherein said probe comprises a first vessel and a second vessel;
    wherein the first vessel and second vessel are connected to a flow inlet and a flow outlet,
    wherein both vessels contain a solid support;
    wherein the solid support comprises a polymer,
    wherein only one of said solid supports has a target immobilized thereto;
    wherein said target is reusable in situ;
    wherein said probe comprises only one detection coil which is arranged around said first and second vessels; and
    wherein the apparatus comprises a first means for generating a pulsed-radio field which at least extends into the first and second vessels of the sample holder, and wherein the apparatus comprises a second means consisting of one or more gradient coils suitably arranged to deliver a pulsed radio field with a linear amplitude gradient along a transverse axis to the first and second vessels.

2. The NMR apparatus according to claim 1, wherein the first means includes one coil suitably arranged to deliver a radio field to the first and second vessels.

3. The NMR apparatus according to claim 1, wherein the polymer is selected from the group consisting of polystyrene, sepharose and agarose resins and gels.

4. A method for identifying compounds that bind to a specific target, the method comprising:
    (a) pumping a sample of interest into a an NMR apparatus, wherein the NMR apparatus comprises a probe; wherein said probe comprises a first sample vessel and a second sample vessel; wherein both sample vessels contain a solid support, wherein the solid support is a polymer;
    wherein only one of said solid supports has a target immobilized thereto, and wherein the sample is pumped into said sample vessels,
    (b) stopping said flow when the sample of interest reaches the first and second sample vessels;
    (c) generating NMR spectra of the sample of interest from the first and second vessels;
    (d) pumping the sample out of the vessels and through the NMR apparatus via a flow outlet;
    (e) reusing said target in situ, and
    (f) analyzing and comparing said NMR spectra to determine differences between said spectra,
    wherein the sample of interest comprises a solution in which one or more compounds being identified for binding are dissolved;
    wherein said first and second spectra are detected at about the same time using the same solution; and
    wherein said probe comprises only one detection coil which is arranged around said sample vessels.

5. The method according to claim 4, wherein the polymer is selected from the group consisting of polystyrene, sepharose and agarose resins and gels.

6. The method of claim 4, wherein the target is a molecule or a collection of molecules.

7. The method of claim 4, wherein the first and second NMR spectra are one-dimensional spectra.

8. The method of claim 4, wherein the first and second NMR spectra are proton-NMR spectra.

9. The method of claim 4, wherein analyzing and comparing said first and second spectra comprises subtracting the first spectrum from the second spectrum, or vice versa.

10. The method of claim 4, wherein analyzing and comparing said first and second spectra comprises determining the areas of the peaks in the first and second spectra and comparing these peak areas.

11. The method of claim 4, wherein said polymer comprises a chromatography resin.

* * * * *